United States Patent

Takeuchi et al.

[11] Patent Number: 5,522,006
[45] Date of Patent: May 28, 1996

[54] ENDOSCOPIC LIGHT SOURCE CONNECTOR

[75] Inventors: Shinji Takeuchi; Haruo Akiba, both of Omiya, Japan

[73] Assignee: Fuji Photo Optical Co., Ltd., Omiya, Japan

[21] Appl. No.: 425,986

[22] Filed: Apr. 20, 1995

[30] Foreign Application Priority Data

Apr. 20, 1994 [JP] Japan .................................. 6-104328
Apr. 20, 1994 [JP] Japan .................................. 6-104329
Apr. 20, 1994 [JP] Japan .................................. 5-104330

[51] Int. Cl.⁶ .................................................. G02B 6/40
[52] U.S. Cl. ........................... 385/139; 385/53; 385/117
[58] Field of Search ............................... 385/53, 54, 88, 385/89, 92, 115, 116, 117, 118, 147, 902, 139

[56] References Cited

U.S. PATENT DOCUMENTS

| | | | |
|---|---|---|---|
| 4,325,606 | 4/1982 | Ikuno et al. ..................... | 385/117 X |
| 4,539,586 | 9/1985 | Danna et al. ..................... | 385/54 X |
| 4,605,280 | 8/1986 | Welber et al. ................... | 385/88 |
| 4,919,621 | 4/1990 | Ams .................................. | 385/92 X |
| 5,101,807 | 4/1992 | Kawashima ..................... | 385/43 X |
| 5,193,135 | 3/1993 | Miyagi ............................. | 385/117 |

*Primary Examiner*—John D. Lee
*Attorney, Agent, or Firm*—Oblon, Spivak, McClelland, Maier & Neustadt

[57] ABSTRACT

A light source connector for disconnectibly connecting an endoscopic light guide to a light source, the connector having a light input end of the light guide fitted in a tubular case of a light guide rod along with a thick rod-like light collecting glass member of high refractivity located directly in face to face relation with a light receiving face at the light input end of the light guide and a thin cover glass member of low refractivity located on the outer side of the thick rod-like glass member.

5 Claims, 3 Drawing Sheets

ENDOSCOPIC LIGHT SOURCE CONNECTOR

BACKGROUND OF THE INVENTION

1. Field of the Art

This invention relates to endoscopes which are in wide use primarily in medical fields, and more particularly to an endoscopic light source connector useful for disconnectibly connecting a light guide of an endoscope to a light source.

2. Prior Art

The endoscopes which are designed to be inserted into dark intracavitary portions of patients for examinations or diagnostic purposes need to be connected to an external light source unit to transmit illuminating light from a source lamp of the light source unit to a particular intracorporeal region under observation through a light guide. For connection to such a light source unit, a light source connector is usually attached to the proximal end of a flexible light guide cable which is extended from a manipulating controller section or main body of an endoscope. Further, in order to transmit the illuminating light from the light source unit down to an illumination window at the distal end of an elongated tubular insert portion of the endoscope, a light guide in the form of a bundle of fiber optics is extended to the illumination window through the flexible light guide cable and the insert portion of the endoscope. The light input end of the light guide is encased in a light guide rod which is protruded from the light source connector and plugged into a socket on the light source unit to connect the light guide thereto.

Since an endoscope is used repeatedly for intracavitary examinations, it must be washed after each use. From a hygienic point of view and for the sake of perfect sterilization, the washing treatment should always include sterilization by the use of a disinfectant. In this regard, for the purpose of enhancing the efficiency of the washing treatment, it has been the usual practice to wash and sterilize an endoscope subsequent to a use by immersing the entire body of the endoscope in a disinfectant liquid for a predetermined time duration, including not only the insert portion of the endoscope but also the manipulating control section and the flexible light guide cable. On such occasions, the light guide rod on the light source connector is susceptible to damages on a light receiving end face of the light guide by contact with the disinfectant liquid particularly in case the light receiving end face of the light guide is in an exposed state.

In this regard, it has been known in the art to protect the light receiving end face of the light guide by fitting a protective glass piece in the light guide rod immediately in front of the light receiving end face of the light guide in such a manner as to provide a hermetically sealed protective cover which keeps the light receiving end face of the light guide from direct contact with a disinfectant washing liquid. In order to guarantee a securer hermetic seal, it is desirable for the cover glass to have an ample seal area on its circumference which engages the inner wall surface of the light guide rod. This requirement has been met by employing a cover glass member which is increased in thickness to such a degree as to generally present a somewhat rod-like shape with an elongated girder portion in the axial direction.

However, a glass cover in the form of an elongated rod-like shape invariably causes a marked drop in light pickup rate at the light receiving end face of the light guide. This is because, of the light rays which are converged toward the light input end of the light guide rod, the light rays of large angles of incidence are allowed to divert toward the inner wall surfaces of the light guide rod without falling directly on the light receiving end face of the light guide. It follows that, in order to let the light rays of large incidence angles reach the light receiving end face of the light guide directly, the protective glass member should desirably have as small a thickness as possible and should have its outer surface located close to the light receiving end face of the light guide. Improvements in these two contradictory requirements, i.e., the hermetic tightness of the cover glass and higher light pickup rate across the cover glass, could be achieved by selecting a glass material of high refractivity for the cover glass. However, high refractivity glass materials are generally inferior in resistance to chemicals and in many cases contain lead or other toxic substances which should be excluded from medical equipments or instruments.

SUMMARY OF THE INVENTION

With the foregoing situations in view, it is an object of the present invention to provide a light source connector for connecting an endoscopic light guide to a light source, the connecting being capable of protecting the light guide in a secure manner and at the same time capable of collecting incident light rays efficiently over a wide angle range, providing secure protection for the light guide against a disinfectant or other chemicals.

It is another object of the present invention to provide a light source connector for connecting an endoscopic light guide to a light source, the connector employing a glass member of high refractivity in such a manner as to transmit illuminating light to the light guide efficiently and substantially free of losses, in combination with means for protecting the high refraction glass member securely against attacks of chemicals.

In accordance with the present invention, the above-stated objectives are achieved by the provision of a light source connector for connecting an endoscopic light guide to a light source, the connector essentially including a light guide rod to be disconnectibly inserted into a socket on the part of the light source and receiving a light input end of the light guide within a tubular case, a thick rod-like glass member of high refractivity securely fitted within the light guide rod case in closely confronting relation with a light receiving end face at the light input end of the light guide, and a thin cover glass member of low refractivity securely fitted within the light guide rod case on the outer side of the thick rod-like glass member of high refractivity.

BRIEF DESCRIPTION OF THE DRAWINGS

The above and other objects, features and advantages of the present invention will become apparent from the following description and the appended claims, taken in conjunction with preferred embodiments of the invention shown by way of example in the accompanying drawings in which:

DESCRIPTION OF PREFERRED EMBODIMENTS

Figure 1:
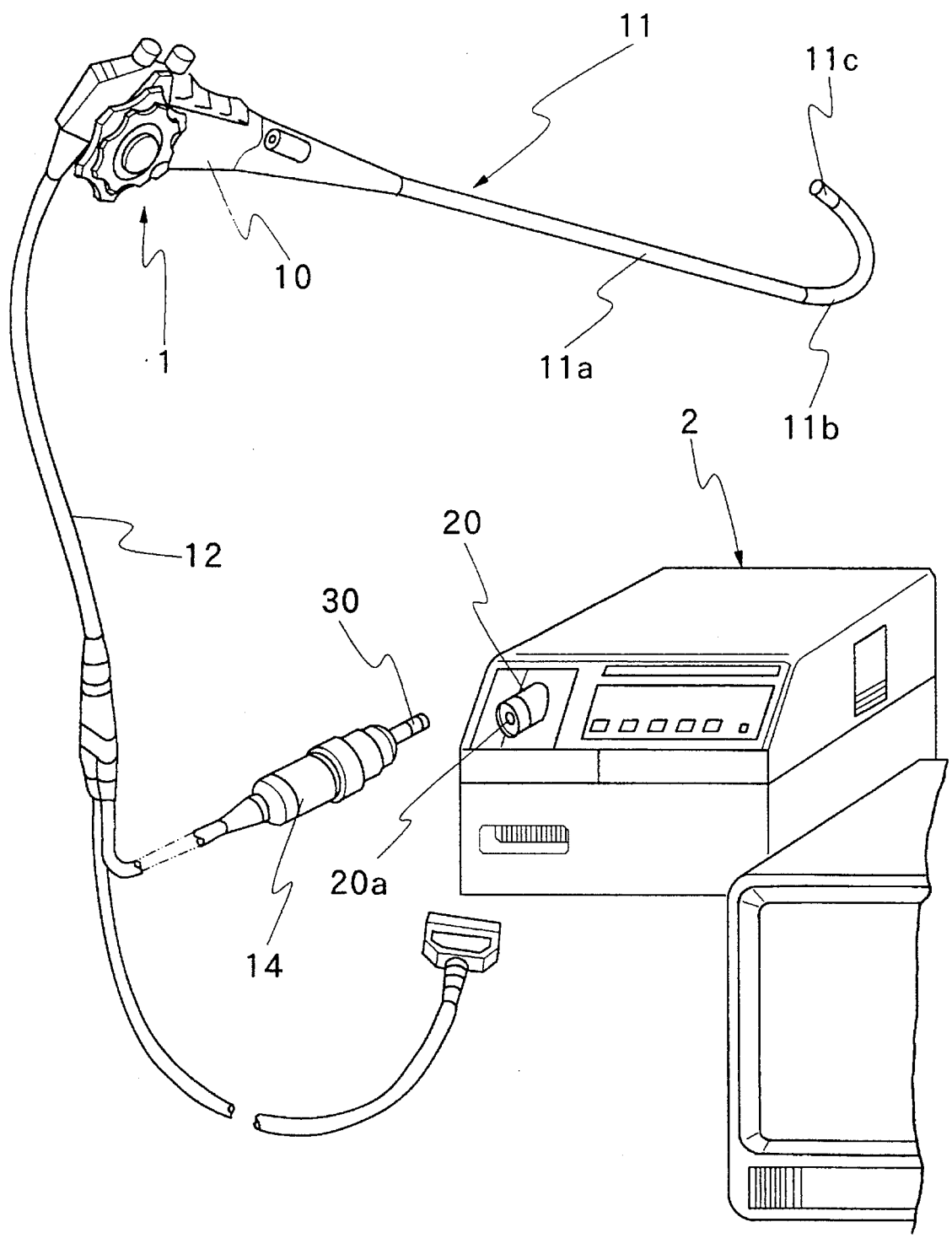
FIG. 1 is a schematic overall view of an endoscope and an external light source unit.
Figure 2:
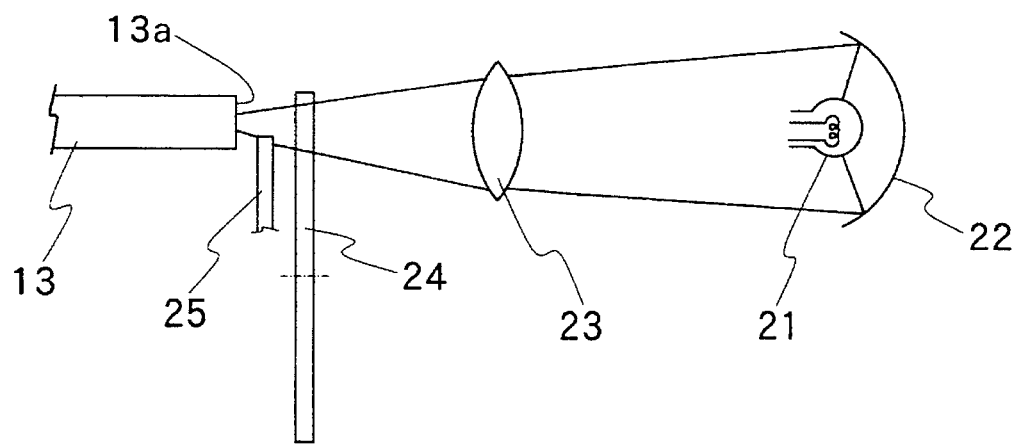
FIG. 2 is a schematic view of a light source connector plugged into the light source unit.
Figure 3:
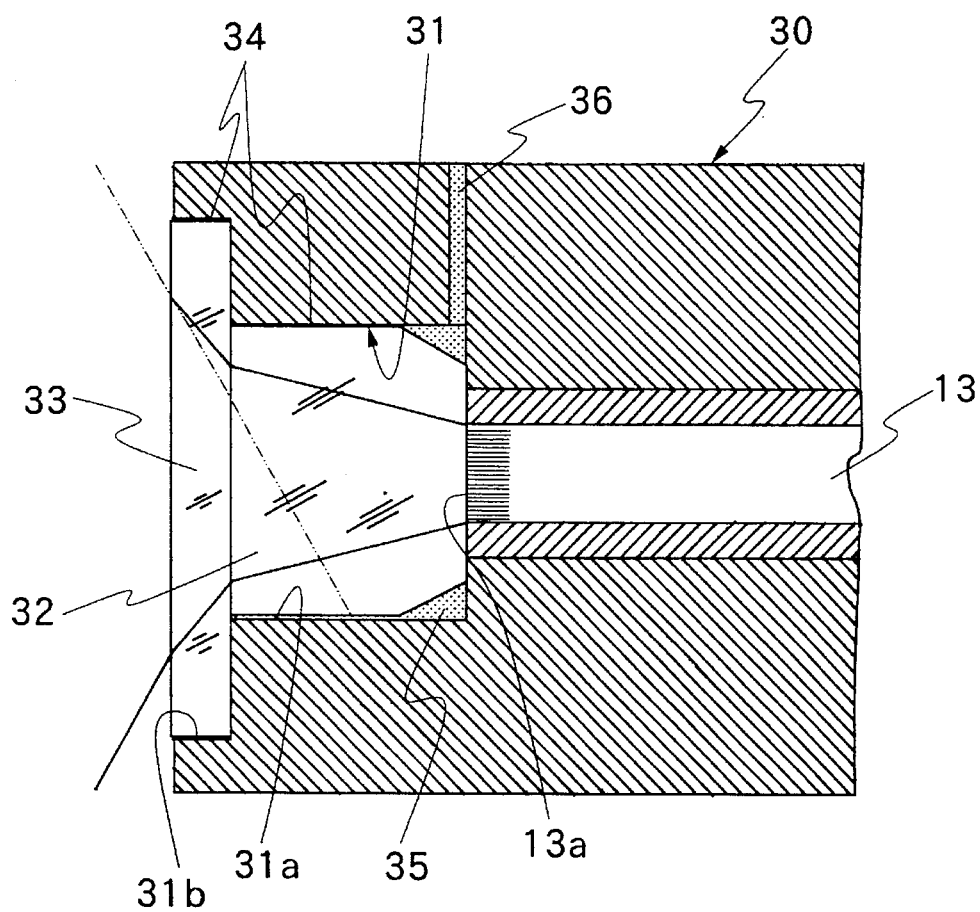
FIG. 3 is a fragmentary sectional view a light source connector according to the invention, showing its major components.
Figure 4:
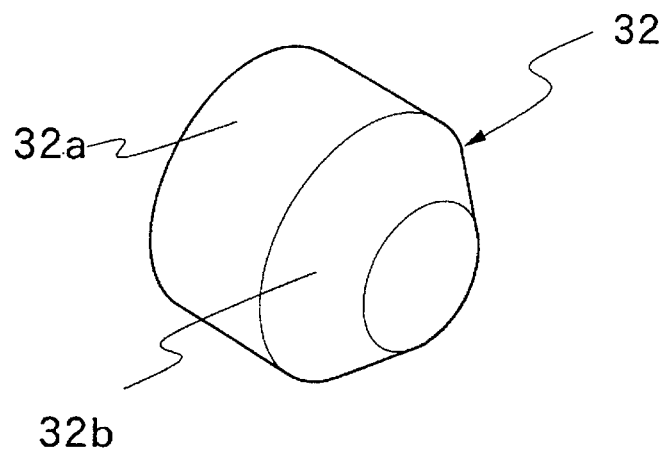
FIG. 4 is a schematic outer view of a light collecting inner glass member.

Referring FIGS. 1 to 3, there is shown a first embodiment of the invention, in which indicated at 1 is an endoscope and at 2 is an external light source unit. The endoscope 1 includes a main body 10 with manipulating control means, a tubular insert portion 11 which is extended on the front side of the main body or manipulating control section 10 for insertion into a patient body, and a flexible light guide cable 12 which is extended on the rear side of the manipulating control section 10 for connection to an external light source unit. The tubular insert section 11 includes a flexible portion 11a which extends almost over the entire length of the insert section 11 from its proximal end which is connected to the manipulating control section 10. An angle portion 11b and a rigid tip end portion 11c are successively connected to the fore end of the flexible insert portion 11a.

The endoscope 1 contains an observation mechanism including an illumination window and an observation window (both not shown) which are provided on the rigid tip end portion 11c in a well known manner. An intracavitary portion of interest, which is under endoscopic observation through the above-mentioned observation window, is irradiated with light which is projected through the illumination window. In case of an electronic endoscope, an objective lens is fitted in the observation window to form an image of the intracavitary portion under observation on a solid-state image sensor device thereby to convert the optical image into electric signals. The electric signals from the solid-state image sensor are processed into video signals by predetermined signal processing operations to display a color video image of the intracavitary portion on a monitor screen M. On the other hand, in case of an optical endoscope, an optical image of an intracavitary portion is picked up by an image guide which is located on the image-forming plane of the objective lens, and transferred through the image guide to an eyepiece which is mounted on the main body of the endoscope. Therefore, the operator can view intracavitary regions of interest through the eyepiece for examination or diagnostic purposes.

The light source unit 2 is provided to supply illuminating light to the intracavitary region under observation, through a light guide 13 which is mounted on the endoscope 1 to transmit the illuminating light with as small transmission losses as possible. The light guide 13 is in the form of a bundle of a multitude of very fine fiber optics, and extends from the proximal end of the flexible light guide cable 12 down to the illumination window at the tip end of the insert portion 11 through the manipulating control section 10 on the main body of the endoscope 1. A light input end 13a of the light guide 13 is fitted into a light guide rod 30 of a light source connector 14 to be disconnectibly plugged into a socket 20 on the light source unit 2 as will be described hereinlater.

As shown in FIG. 2, a lamp 21 is mounted internally of the light source 2 as a source of illuminating light. The illuminating light from the source lamp 21 is reflected on a concave reflector mirror 22 and converged toward the input end 13a of the light guide 13 through a condenser lens 23 which is located substantially at the focal point of the reflector mirror 22. Indicated at 24 is a rotating tri-color filter at which the illuminating light is sequentially passed through color filter zones of red, green and blue wavelengths, each separated by a blanking zone, for sequentially irradiating light of red, green and blue wavelengths in case of an electronic endoscope with a solid-state image sensor device driven by a sequential color scanning system. Denoted at 25 is a light volume member for adjusting the input light level. The just-mentioned rotating color filter 24 and light volume member 25 are used only with an electronic endoscope, and are normally unnecessary in case of an optical endoscope.

The light guide rod 30 which is projected from end of the connector 14 is placed into a receptacle cavity 20a of the socket 20 on the light source 2 to connect the light guide 13 thereto. As seen in FIG. 3, the light guide rod 30 has the light guide 13 fixedly fitted in a tubular case in such a way that the input end 13a of the light guide is located in a predetermined position within the tubular case. Further, the light guide rod 30 is provided with a glass fitting stepped wall portion 31 on the inner periphery and at the distal end of its tubular case, the glass fitting stepped wall portion 31 defining an inner glass-seating cavity 31a of a smaller diameter for fitting an inner light collecting glass member 32 and an outer glass-seating cavity 31b of a larger diameter for fitting an outer cover glass member 33 immediately on the outer side of the inner light collecting glass member 32. In this instance, the inner glass member 32 is formed in a rod-like shape as a whole because of its large thickness in the axial direction and in a circular or polygonal shape in cross-section, and formed of a glass material of high refractivity in optical properties. On the other hand, the outer cover glass member 33 of a thin disc-like shape is formed of a glass material of low refractivity.

The light rays from the source lamp 21, which are incident on the outer surface of the cover glass member 33, are successively passed through the cover glass member 33 and the inner glass member 32 to fall on the light receiving face at the light input end 13a of the light guide 13. Therefore, from the standpoint of light collecting efficiently, it is advantageous to locate the light incident outer surface of the cover glass 33 at as small a distance as possible from the light input end 13a of the light guide 13. Namely, it is preferred that the outer cover glass member 33, the inner glass member 32 and the light receiving end face 13a be disposed in intimately contacting relations with each other. However, should a narrow air gap exist between them, it would not impair the functions of the respective glass members to any material degree.

The inner high refraction glass member 32 is fixedly bonded in the smaller cavity 31a on the inner periphery of the light guide rod 30 through an adhesive sealing material 34. Since this inner glass member 32 is in a rod-like shape having a large thickness in the axial direction as mentioned hereinbefore, it has a very broad sealing area around and along its circumference. As a consequence, the inner glass member 32 can form a secure hermetic seal over a broad area in cooperation with the inner peripheral wall of the smaller cavity 31a of the light guide rod 30 for protecting the light guide 13 in a very reliable manner. Even if the connector 14 is immersed in a disinfectant liquid at the time of washing the endoscope 1, it can perfectly block intrusion of not only the disinfectant liquid but also its vapors.

The inner glass member 32 is formed of a high refraction glass material as mentioned hereinbefore. Even through not more than the light guide 13, the glass material of this sort is usually more or less inferior in resistance to chemicals so that, if brought into direct contact with a disinfectant, it is very likely for its surfaces to get frosted by attacks of the disinfectant, suffering from losses in light transmittance to a considerable degree. However, the inner high refraction glass member 32 is protected against attacks of chemicals by the low refraction cover glass member 33, which is fixedly fitted in the larger cavity 31b by the use of a sealing material 34 immediately on the outer side of the inner high refraction glass member 32. Under the protection by this cover glass member 33, the inner high refraction glass member 32 is securely kept from direct contact with the disinfectant liquid at the time of washing the endoscope. The cover glass member 33 may be of an ordinary quartz glass sheet which has high resistance to chemicals along with high immunity from deteriorations, damages or degenerations as caused by direct contact with a disinfectant liquid.

By the provision of the inner glass member 32 which has a large thickness in the axial direction, the light receiving face at the light input end 13a of the light guide 13 is naturally located in a position which is axially spaced from the outer light incident surface of the cover glass member 33. However, the cover glass member 33 has a larger diameter as compared with the inner high refraction glass member 32. Therefore, of the light rays which are projected from the source lamp 21, even the light rays which are shed on the outer cover glass member 33 at relatively large angles of incidence are bent and passed on toward the light receiving face at the light input end 13a of the light guide 13 by the action of the high refraction glass member 32, to fall directly on the light receiving face 13a of the light guide 13 instead of travelling toward the inner periphery of the light guide rod 30. As a result, the illuminating light rays from the source lamp 21 can be collected by the light guide 13 efficiently over a wide angle range to increase the volume of light transmission. It follows that the subject under endoscopic observation can be illuminated with a greater amount of light.

The above-described inner glass member 32 which is fitted in the smaller cavity 31a may be in the shape of a circular or polygonal cylinder as a whole. However, the inner glass member 32 is preferred to have a circular cylindrical body 32a of a predetermined length in the axial direction, the circular cylindrical body 32a being tapered into a truncated cone shape at its inner end 32b to be mounted in face to face relation with the light input end 13a of the light guide 13. The main cylindrical body 32a of the inner glass member 32 has a diameter which is slightly smaller than the inside diameter of the inner cavity 31a so that, when mounted in position, it is intimately engaged with the latter through the sealing material 34. The end face of the truncated cone-shaped inner end 32a of the inner glass member 32 is arranged to have an outside diameter which is larger than that of the light pickup end face 13a of the light guide 13 in an ample degree, and substantially held in intimate contact with the latter.

The inner glass member 32 of the above-described arrangements is firstly placed into the smaller diameter cavity 31a which has the sealing material 34 applied on the entire inner wall surface thereof. In this regard, it is desirable to coat the sealing material 34 uniformly on the entire inner wall surface of the cavity 31a and, for the purpose of enhancing the hermetic tightness of the seal, to coat the sealing material 34 in a slightly excessive amount. The inner glass member 32 is fitted into the smaller diameter cavity 31a from its truncated cone-shaped inner end 32b. The end face of the truncated cone-shaped end 32b which is distinctively smaller than the inside diameter of the smaller cavity 31a can be inserted into the latter quite easily. As soon as the truncated cone-shaped end 32b of the inner glass member 32 is completely placed into the smaller cavity 31a, the cylindrical body portion 31a can be securely fitted into the smaller cavity 31a which has a slight diametral differential from the cylindrical body portion 32a.

As the cylindrical body portion 32a of the inner glass member 32 is fitted into the smaller cavity 31a, excess part of the coated sealing material 34 on the inner wall surface of the smaller cavity 31a is pushed toward the inner end of the cavity 31a. However, since the tapered inner end 32b of the glass member 32 is gradually spaced away from the inner wall surface of the smaller cavity 31a, the pushed excess sealing material 34 is trapped in a space 35 between the tapered inner end 32b and the inner wall surface of the smaller cavity 31a, free of possibilities of being pushed onto the end face of the tapered inner end 32b of the glass member 32. The light guide rod 30 is provided with an air escape hole 36 in its case in communication with the trapping space 35, thereby preventing air in the space 35 from being compressed into a closed space to increase the resistance to insertion of the inner glass member 32 or to produce air bubbles in the sealing material 34.

Figure 5:
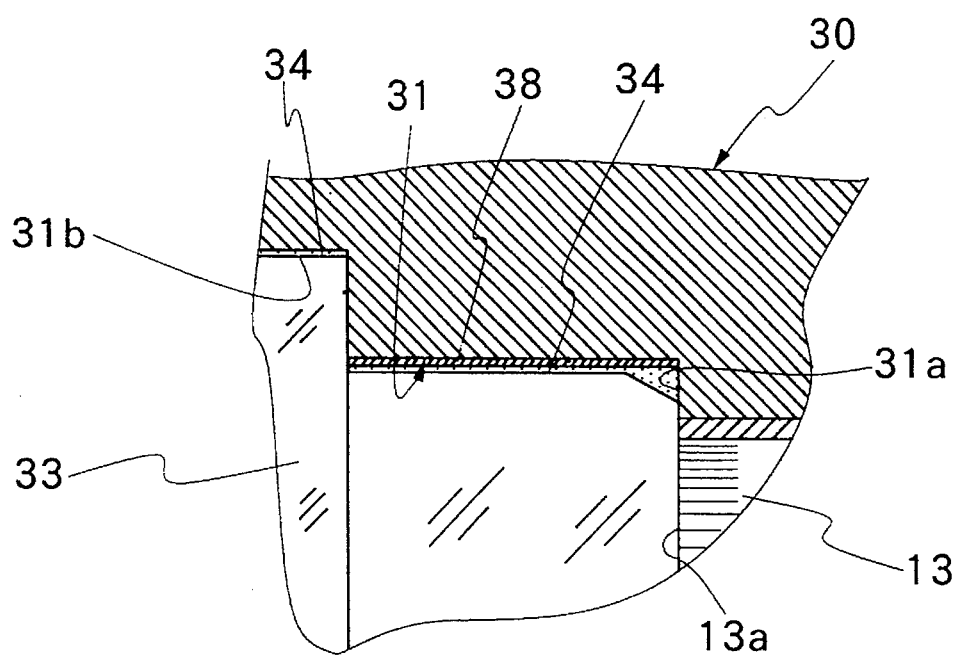
FIG. 5 is a fragmentary sectional view on an enlarged scale of the light source connector of the invention, showing details of its major components.

As illustrated in FIG. 5, there may be provided a light reflector film layer 38 on its inner wall surface, while selecting as the sealing material 34 a composition of extremely high transparency such as, for example, KE-41T liquid type RTV rubber (a tradename for a product manufactured by Shin-Etsu Chemical Industry Co., Ltd.). The light which comes in through the outer glass member 33 reaches the light receiving end face 13a of the light guide 13 not only by direct transmission through the inner glass member 32 but also after a certain number of repeated reflections across the glass member 32. In case the sealing material 34 between the inner glass member 32 and the inner wall surface of the smaller cavity 31a has high transparency, the light rays coming in at large angles of incidence toward the inner wall surface of the smaller cavity 31a are almost completely passed through the transparent sealing material 34 and reflected off on the coated reflector film layer 38 on the inner wall surface and returned into the glass member 32 substantially in the fashion of total reflection. Accordingly, by reflections within the inner glass member 32, even light rays of large angles of incidence are transmitted to the light guide 13 with only minimum losses. Namely, the above-described arrangements make it possible to transmit the illumination light from the source lamp efficiently with the least loss to suppress the light attenuation to a minimum.

In FIG. 3, for example, if the light guide rod 30 employs HOYA.FD6 (a tradename) with a refractivity (nd)= 1.80518 and a thickness of 10 mm for the inner glass member 32, quartz glass with a refractivity (nd)=1.45857 and a thickness of 2 mm for the outer cover glass member 33 in combination with the light guide 13 having a diameter of 3.5 mm at its light input end face 13a, a light ray coming from the light source at an angle of incidence of 60° is firstly refracted in the outer cover glass member 33 to enter the inner glass member 32 at an angle of 36.7° and refracted again in the glass member 32 through 28.65°. Therefore, the light ray which enters the outer cover glass member 33 at an angle of 60° is securely directed toward the light input end face 13a of the light guide 13 as indicated by a solid line instead of advancing toward the inner wall surface of the light guide rod 30 as indicated by an imaginary line. As a consequence, the incident light rays are efficiently collected at the light input end face 13a to increase the volume of light transmission through the light guide 13. In case the light guide 13 has a numerical aperture (NA) of 0.87, it can transmit incident light rays efficiently up to an angle of incidence of 60° at the maximum. Besides, in case the glass member 32 has a thickness of as large as 10 mm, a sufficient sealing area can be secured around its circumference. This means that the light input end 13a of the light guide 13 can be retained strictly in a hermetically sealed state under secure and effective protection.

What is claimed is:

1. A light source connector for connecting an endoscopic light guide to a light source, said connector comprising:

a light guide rod to be disconnectibly inserted into a socket provided on said light source and receiving a light input end of said light guide within a tubular case;

a thick rod-like glass member of high refractivity securely and hermetically fitted within said case of said light guide rod in closely confronting relation with a light receiving face at said light input end of said light guide; and a thin cover glass member of low refractivity securely fitted within said case of said light guide rod on the outer side of the thick rod-like glass member of high refractivity.

2. A light source connector as defined in claim 1, wherein said rod-like glass member has a predetermined thickness in the axial direction and is tapered to have a gradually diminishing sectional area at the inner end confronting said light receiving face of said light guide, said rod-like glass member having a larger diameter than said light receiving face of said light guide at said tapered inner end and being hermetically fitted in said case of said light guide rod through a sealing material.

3. A light source connector as defined in claim 2, wherein said rod-like glass member is provided with a body of a circular cylindrical shape and a tapered inner end of a truncated cone shape with an end face larger in diameter than said light receiving face at the light input end of said light guide, said rod-like glass member being fixedly and hermetically fitted in a glass seating cavity on the inner periphery of said light guide rod through a sealing material with said truncated cone-shaped inner end in closely confronting relation with said light receiving face of said light guide.

4. A light source connector as defined in claim 3, wherein said case of said light guide rod is provided with an air escape hole in communication with a space to be formed between said truncated cone-shaped inner end of said rod-like glass member and inner wall surfaces of said cavity.

5. A light source connector as defined in claim 3, wherein said case of said light guide rod is provided with a light reflector film layer on inner wall surfaces of said glass seating cavity, and said rod-like glass member is securely and hermetically fitted in said cavity through a transparent sealing material.

* * * * *